United States Patent [19]
Guthrie et al.

[11] Patent Number: 6,003,386
[45] Date of Patent: Dec. 21, 1999

[54] DISPOSABLE MASS FLOW TRANSDUCER

[75] Inventors: Robert Guthrie, Ventura; John Yan, Sunnyvale, both of Calif.; Rene Luigies, Bilthoven, Netherlands

[73] Assignee: Becton, Dickinson and Company, Franklin Lakes, N.J.

[21] Appl. No.: 09/111,538

[22] Filed: Jul. 8, 1998

Related U.S. Application Data

[62] Division of application No. 08/962,228, Oct. 31, 1997.

[51] Int. Cl.[6] .................................................. G01F 1/34
[52] U.S. Cl. ........................................................ 73/861.42
[58] Field of Search ............................ 73/861.02, 861.53, 73/861.42, 861.72, 863.02, 863.03, 863.61, 756, 196; 137/460, 487; 374/36, 37

[56] References Cited

U.S. PATENT DOCUMENTS

| | | | |
|---|---|---|---|
| 4,969,364 | 11/1990 | Masuda | 73/861.72 |
| 5,201,581 | 4/1993 | Vander Heyden et al. | 73/196 |
| 5,323,657 | 6/1994 | Vander Heyden et al. | 73/861.02 |
| 5,889,212 | 3/1999 | Guthrie et al. | 73/720 |

*Primary Examiner*—William Oen
*Attorney, Agent, or Firm*—Eric M. Lee

[57] ABSTRACT

A single, disposable differential transducer having a molded plastic body in which there is a pair of chambers separated by a strain gage electronic chip that flexes in accordance with the difference in the pressures between the two chambers. The plastic housing has inlets to allow communication with the chambers and the overall unit is readily manufactured of inexpensive components that allow disposability of the unit when it has been used on a patient. The pressure transducer chambers are isolasted from each other such that differing locations of the patient may be sensed for pressure at the same time without the risk of inadvertant cross-contamination.

4 Claims, 3 Drawing Sheets

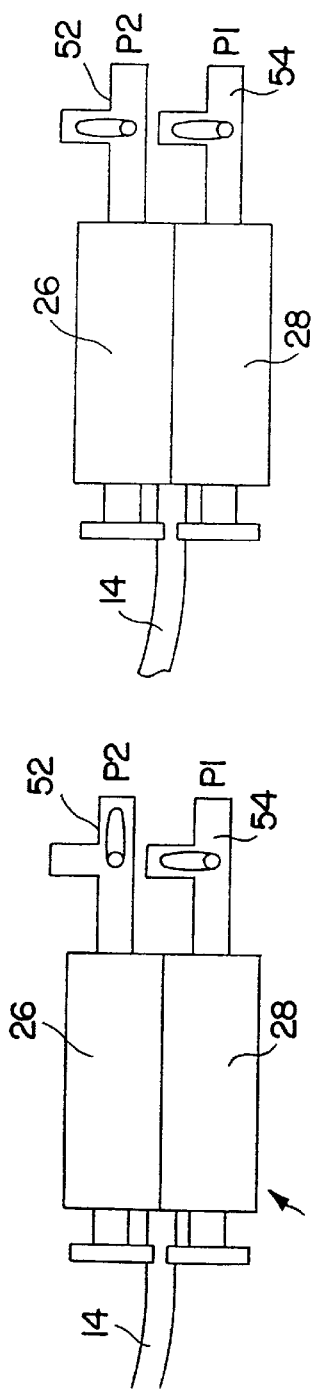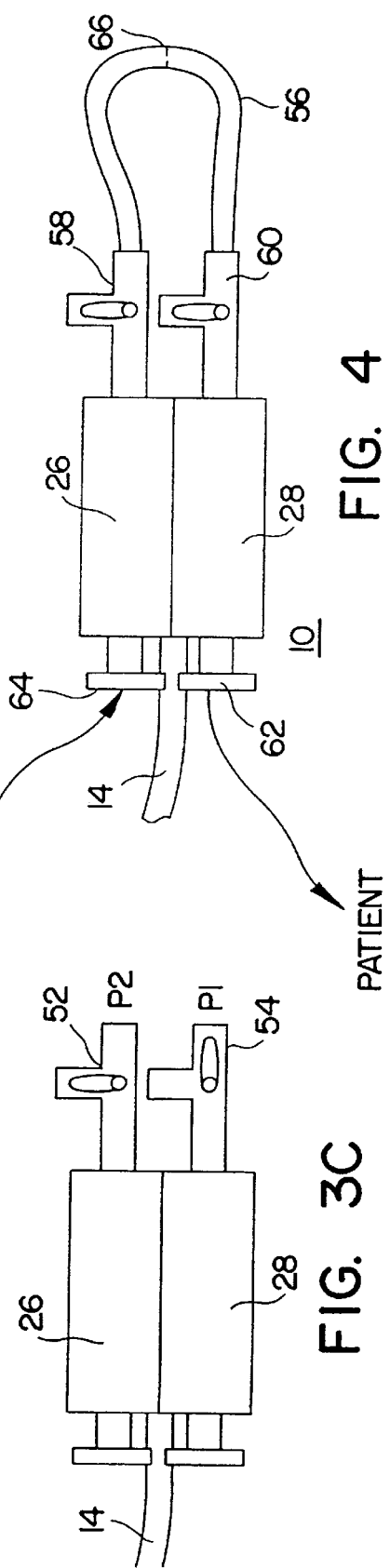

DISPOSABLE MASS FLOW TRANSDUCER

This application is a division of 08/962,228, filed Oct. 31, 1997.

BACKGROUND OF THE INVENTION

The present invention relates to a pressure transducer and, more particularly, to a disposable pressure transducer that can be used to measure pressure gradients, relative pressure and mass flow rate.

There are currently a number of disposable pressure transducers on the market, particularly, for the measurement of the blood pressure in a human patient in various hospital environments. Such blood pressure disposable transducers are shown and described in U.S. Pat. Nos. 4,576,181; 4,610,256; 4,679,567 and 5,015,256. As can be seen, such pressure transducers rely upon a special strain gage chip that is positioned within the plastic housing and which is commercially produced for such applications.

In such present blood pressure transducers, typically the chip is positioned between a chamber that sees the blood pressure of the patient to be measured and a chamber that is open to the atmosphere so that the absolute pressure is read by the chip as it flexes due to the changes in the patients blood pressure.

There is a need for a disposable differential pressure transducer since there are many occasions when the difference in pressure between two supra or subatmospheric pressures are involved and a determination needed as to that differential. At the present, such differential pressure transducers are rather expensive and the construction not adapted to the inexpensive, throw-away variety.

In particular, at the present, disposable pressure transducers are used to determine the blood pressure of a patient at two differing locations by running separate lines to the locations where the pressure is to be measured and those lines communicating to a single disposable pressure transducer through a series of stopcocks where either pressure line may be selected. As a continuing problem with such measurements, it is possible to inadvertently misposition the stopcocks such that the pressure transducer is shunted out of the circuit and the two separate locations within the patient are actually connected to each other.

Therefore, there is a need for an inexpensively constructed differential pressure transducer for uses where the difference in two pressure levels is desired, where neither of the pressures need be atmospheric pressure.

SUMMARY OF THE INVENTION

In accordance with the present invention, a differential pressure transducer is provided and which is usable to measure differential pressures and which is also capable of inexpensive production and thus may be disposable after use.

The differential pressure transducers makes use of the inexpensive chip currently used in blood pressure transducers and locates that chip in an inexpensive plastic body having ports for the sensing of two differing pressures where neither pressure need be atmospheric.

Accordingly, the present pressure transducer can be used in applications in any location where the transducer cannot be readily cleaned and maintained in its environment since the transducer can be readily disposed of after a single use.

The differential pressure transducer is comprised of an inexpensive molded plastic housing, preferably molded in two pieces and joined together. The normal chip currently available on a mass production basis is used and which is seated in the plastic housing such that it basically divides the plastic housing into two chambers, each of which are communicating with various pressures to be measured through ports formed in the plastic housings.

The differential pressure between those two chambers is thus sensed by the chip and that differential pressure is communicated to a suitable monitor through electrical wires from the chip to a lead wire extending from the plastic housing.

Thus, two pressures can be sensed through the communication input ports and those pressures are communicated to two chambers within the plastic housing and the chip, located intermediate the chambers, can detect and communicate the differential pressure between those chambers to a monitor to display that pressure differential. Neither of the pressures, therefore need be atmospheric as is required in the current disposable pressure transducers.

Each chamber is electrically isolated from the chip itself by means such as a silicone gel so that each chamber may be used to measure pressures within a patient and, to facilitate connection to patient lines and the like, both chambers are accessible by means of Luer fittings that provide ease of connection with normal patient lines. Accordingly, the housing encloses two chambers capable of individually measuring positive or negative pressure so as to determine the differential pressure therebetween.

Either of the chambers can be opened to the atmosphere while the other is connected to the patient line. This allows either continuous or intermittent pressure measurement with one transducer.

In addition, since each chamber is effectively isolated from the other, the differential pressure transducer can safely be used with patient lines where two differing locations within the patient are being measured. Each patient line can be connected to the differential pressure transducer by the separate chambers and the possibility of a shunting of the pressure transducer is avoided since it is not necessary to have any fluid lines that join the separate patient pressure lines.

Further, the differential pressure transducer of the present invention can easily and effectively be used to determine the mass flow rate of blood within the patient at selected locations such as, for example, by measuring the pressure gradient between certain locations such as the left atrium and the left ventricle as will be explained. As an alternative, the differential pressure transducer can also effectively be used to determine the mass flow rate of fluids administered to the patient, such as I.V. fluids by inserting the transducer into the fluid line of the fluid being provided to that patient.

All of the foregoing operational principles and advantages of the present invention will be more fully appreciated upon consideration of the following detailed description, with reference to the appended drawings.

BRIEF DESCRIPTION OF THE DRAWINGS

FIGS. 3A–3C are schematic views showing various configurations in which the differential pressure transducer of the present invention can be used; and FIG. 4 is a further schematic view of a differential pressure of the present invention showing a further use thereof.

DETAILED DESCRIPTION OF THE PREFERRED EMBODIMENT

Figure 1:
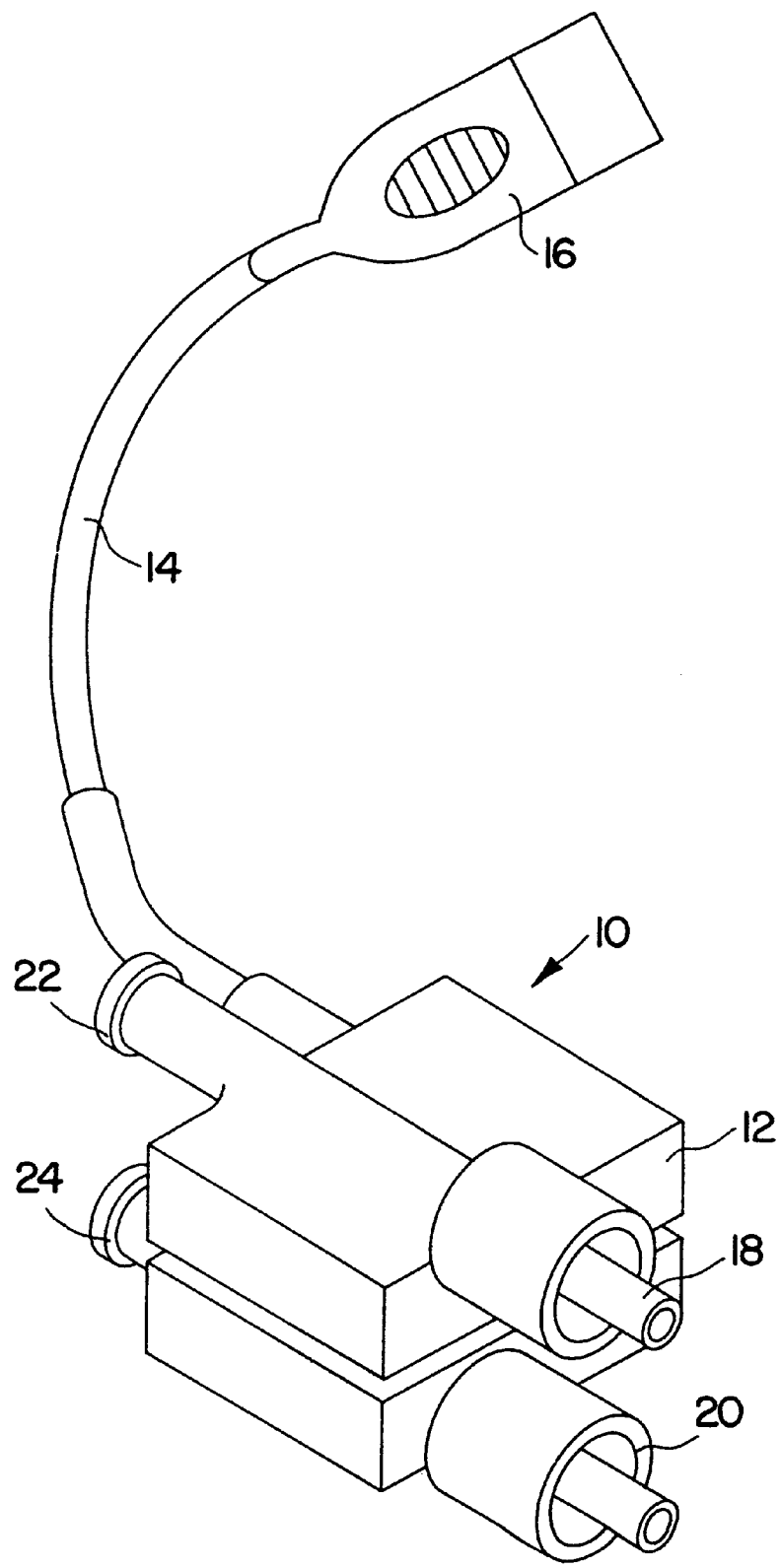
FIG. 1 is an isometric view of a differential pressure transducer constructed in accordance with the present invention.

Turning first to FIG. 1, there is shown an isometric view of a differential pressure transducer 10 constructed in accordance with the present invention. The differential pressure transducer includes a housing 12 that is preferably injection molded of a plastic material such as polycarbonate and is readily produced through high volume, low cost production methods. Preferably, the plastic material is transparent to allow the user to view the inside of the transducer to verify that the passageways are clear of impediments or air bubbles.

Extending from the housing 12 is an electrical cable 14 that ends in a plug 16 for connection to a cable of a monitor for displaying differential pressure detected by the differential pressure transducer 10.

Luer fittings are included on the housing 12 and preferably include female Luer fittings 18, 20 and male Luer fittings 22, 24 such that the differential pressure transducer 10 may be attached to normal fluid lines used in the medical environment, and are adaptable to be connected to male Luer fittings, female Luer fittings or both where a continuous path of the fluid passes through the differential pressure transducer 10.

Figure 2:
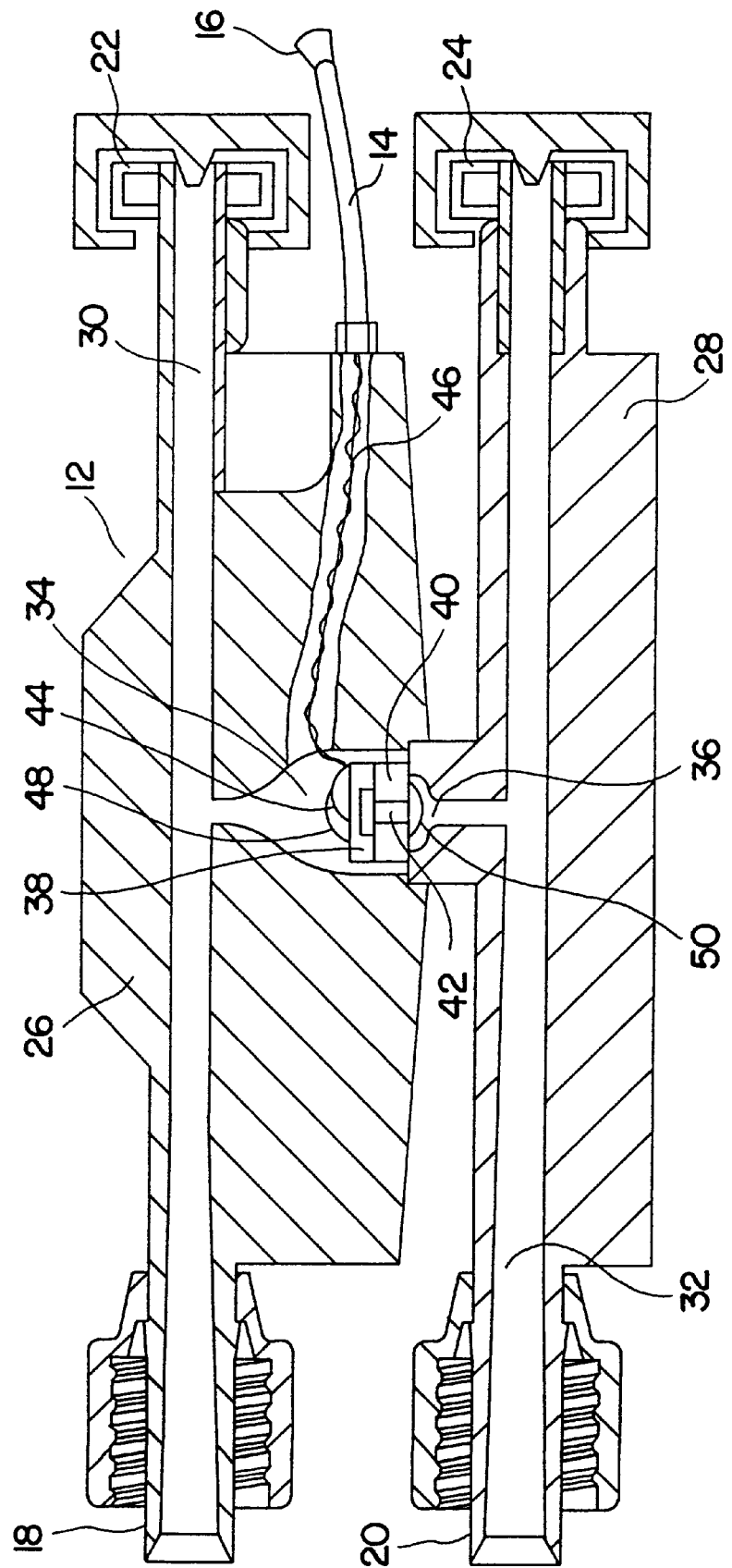
FIG. 2 is a side cross-sectional view of the differential pressure transducer of FIG. 1.

Turning now to FIG. 2, there is shown a side cross-sectional view of a differential pressure transducer 10 of FIG. 1. As can be seen, the housing 12 is preferably injection molded in two sections, comprising an upper section 26 and a lower section 28 and, as will be explained, the two sections are bonded together to create the overall housing 12.

Within housing 12, there is formed a through passageway 30 extending between the male Luer fitting 22 and the female Luer fitting 18 in the upper section 26 and a further through passageway 32 similarly extending between male Luer fitting 24 to female Luer fitting 20 in the lower section 28. Accordingly, there are two through passageways for fluid to pass through the differential pressure transducer 10 or for one or more fluid lines to be attached thereto.

A first chamber 34 is formed in the housing 12 in the upper section 26 and which communicates with the through passageway 30. Again, in similar design, a second chamber 36 is formed in the housing 12 in the lower section 28 and which communicates with through passageway 32.

Both the first and second chambers 34, 36 meet within the housing 12, however, actual communication between the chambers 34, 36 is prevented by the presence of a pressure sensing means. As shown in the FIG. 2, the pressure sensing means is preferable a chip 38 of conventional design, one of which is readily available commercially from Lucas Novasensor Company of Fremont, Calif. The chip 38 is preferable located on a cylindrical wafer 40 which may be of a ceramic material and which has a passage 42 which allows the second chamber 36 to communicate with the underside of the chip 38 to communicate pressure within the second chamber to the chip 38.

Similarly, the upper surface of the chip 38 sees the pressure within the first chamber 34 and the chip 38 therefore flexes in accordance with the differential pressure between the first and second chambers 34, 36. Conventional wiring may be used, such as gold bonding wires 44 to contacts on the chip 38 and which are then connected to wires 46 leading to the external cable 14 and to the plug 16 for connecting to a cable of a monitor.

Accordingly, as can be seen, the chip 38, or pressure sensing means may be a conventional electronic chip 38 that is commercially available and inexpensive. By mounting that chip 38 intermediate the chambers 34 and 36, the chip detects the differential pressure between those chambers and, obviously, the pressure differential between the through passageways, 30 and 32.

Both surfaces of the chip 38 are generally protected by an insulating means to prevent electrical conduct between the fluid in either of the chambers 34, 36 and the chip 38. Such isolating means may be a material having a high dielectric strength, such as silicone gel 48, 50 covering the chip 38 or may comprise a coating of other, high dielectric strength, nonconductive materials including paralyne or polytetraflouroethylene.

Thus, the overall unit is manufactured of inexpensive components; the housing 12 is injection molded in two pieces, an upper section 26 and a lower section 28 which are joined together by various means of bonding. Typical bonding means include the use of solvents such as trichloromethane, THF or by adhesives such as U.V. adhesive, hot melts, cyanoacrylate or by RF heating or ultrasonic welding.

The chip 38 is easily manufactured by conventional processes and can be mounted in its position by high volume mass production techniques similar to the techniques used to manufacture current disposable pressure transducers, yet the unit is capable of detecting the differential pressures between fluids introduced into any two or more sets of the inlets to the differential pressure transducer 10.

As an example of the versatility of the differential pressure transducer 10, in FIGS. 3A–3B, there is shown a schematic of various arrangements of the differential pressure transducer 10 of the present invention. As can be seen, stopcocks 52 and 54 are added to the differential pressure transducer 10 and which may be located at the male or female Luer fittings. The other Luer fittings are closed for purposes of the illustration.

In FIG. 3A, the stopcock 52 is in the closed position and the stopcock 54 is in the open position. Accordingly, the differential pressure transducer 10 is capable of acting as a normal disposable pressure transducer and will read the pressure in the lower section 28, for example P1.

In the FIG. 3B illustration, both stopcocks 52 and 54 are open such that the differential pressure transducer 10 is connected to the fluid through both stopcocks and therefore the differential pressure transducer 10 will indicate the difference in pressure between the chambers (not shown) in the upper section 26 and the lower section 28 to read the differential pressure of the fluids connected to the stopcocks 52 and 54 (P1–P2).

In FIG. 3C, the stopcock 52 is now open and the stopcock 54 is closed, therefore as explained with respect to FIG. 3A, the differential pressure transducer 10 can read the pressure in the chamber within the upper section 26 or P2.

Finally, in FIG. 4, there is shown a schematic view of the differential pressure transducer used to determine mass flow rate. As shown, the differential pressure transducer 10 includes a loop of fluid tubing 56 that interconnects between the chambers of the upper section 26 and the lower section 28 and that connection may include stopcocks 58 and 60. The other connections 62 and 64 to the chamber of the upper section 26 and the lower section 28, respectively, are connected to the fluid to be measured.

In the example of FIG. 4, the differential pressure transducer 10 is shown as measuring an I.V. fluid being administered to a patient and therefore the connection 62 is connected to a line leading to the patient (not shown) and the connection 64 is connected to a source of I.V. solution by means of a hung I.V. bag, I.V. pump, pressurized bag or the like.

A small orifice 66 is provided in the loop of fluid tubing 56 as a fixed resistance, or, as an option, may be a variable orifice, and the mass flow is determined by the equation of Poisielle's Law $$Q = \Delta P / R$$

where $\Delta P$ is the differential pressure measured by the differential pressure transducer and R is the flow resistance. By this means, the disposable differential pressure transducer provides an inexpensive measurement of flow of an I.V. device to the patient and which can readily be disposed after a single use. As can be seen, other flow rates can as easily be determined by communicating connections 62 and 64 to other fluids.

Such fluids can even include blood within the patient by connecting, for example, a patient line having a distal end within the left ventricle and another patient line within the left atrium to the connections 62 and 64 and thus blood flow in the patient can be readily measured.

Therefore, by the present differential pressure transducer 10, one may measure the pressure in any one patient line, similar to the current use of disposable pressure transducers, however, an added dimension is present since the same transducer can, at approximately the same manufacturing costs, now also measure the differential in two patient streams with still providing protection to the patient and with the same accuracy as the current single pressure disposable transducers or determine the mass flow rate of fluids within the patient or administered to the patient.

We claim:

1. A disposable mass flow transducer for measuring the flow of a fluid, said transducer comprising a plastic molded housing, said housing having formed therein, first and second chambers isolated from each other, first and second ports formed in said housing and communicating with said first chamber, third and fourth ports formed in said housing and communicating with said second chamber, a pressure responsive electronic chip mounted in said housing intermediate said first and said second chamber and preventing fluid communication between said first and said second chambers, electrical isolating means adjacent each side of said chip to electrically isolate fluid contained in said first and second chamber from said chip, conduit means communicating between said first and third ports, said conduit means having a known resistance to the flow of fluid through said conduit means, said second and fourth ports adapted to be connected to the fluid whereby the fluid flows through both said first and said second chambers, means to measure and indicate the amount of flexing of said chip to determine the differential in pressure between said first and said second chambers, and means to determine the mass flow of the fluid passing through said mass flow transducer by the differential pressure measured and said known resistance.

2. A disposable mass flow transducer as defined in claim 1 wherein said known resistance comprises a variable resistance.

3. A disposable mass flow transducer as defined in claim 1 wherein said known resistance comprises a fixed orifice.

4. A disposable mass flow transducer as defined in claim 1 wherein said pressure responsive chip comprises a strain gage.

* * * * *